United States Patent
Wen et al.

(10) Patent No.: US 7,291,828 B2
(45) Date of Patent: Nov. 6, 2007

(54) MEASURING SYSTEM FOR DETERMINING THE ELECTROMECHANICAL COUPLING CHARACTERISTICS OF A PZT VIBRATOR

(75) Inventors: Chao-Chun Wen, No.5, Lane 185, Wunlin Rd., Zhudong Town, Hsinchu County 31045 (TW); Fuh-Liang Wen, Hsinchu (TW)

(73) Assignee: Chao-Chun Wen, Hsinchu (TW)

( * ) Notice: Subject to any disclaimer, the term of this patent is extended or adjusted under 35 U.S.C. 154(b) by 127 days.

(21) Appl. No.: 11/313,667

(22) Filed: Dec. 22, 2005

(65) Prior Publication Data
US 2007/0144271 A1  Jun. 28, 2007

(51) Int. Cl.
  *H01J 40/14* (2006.01)
  *G10K 10/00* (2006.01)
(52) U.S. Cl. .................................. 250/222.1; 73/570.5
(58) Field of Classification Search ............... 250/221, 250/222.1; 73/12.02, 12.04, 12.08, 12.12, 73/570.5, 571; 356/614
See application file for complete search history.

(56) References Cited

U.S. PATENT DOCUMENTS

| | | | | |
|---|---|---|---|---|
| 4,006,626 A | * | 2/1977 | Ruzicka et al. | 73/12.02 |
| 4,097,800 A | * | 6/1978 | Kuchmas et al. | 324/178 |
| 4,509,362 A | * | 4/1985 | Lyons | 73/79 |
| 4,520,656 A | * | 6/1985 | Barmatz et al. | 73/570.5 |
| 4,549,435 A | * | 10/1985 | Barmatz et al. | 73/570.5 |
| 5,102,226 A | * | 4/1992 | Yoshimura et al. | 356/602 |
| 5,245,862 A | * | 9/1993 | Zeiss | 73/79 |
| 2004/0206156 A1 | * | 10/2004 | Barr | 73/12.01 |

* cited by examiner

Primary Examiner—John R. Lee

(57) ABSTRACT

A measuring system for determining the electromechanical coupling characteristics of a piezoceramic (PZT) vibrator, which apply photo-interrupters matrix, glass tube, and metal ball to measure the bouncing motion, wherein the system includes an elastic-bouncing tester, a height measuring circuit, an instantaneous height indicator, a microprocessor, a monitor, and a driving circuit. There is a metal ball in the elastic-bouncing tester. By measuring the bouncing height and flying time, it can determine the electromechanical coupling characteristics of a PZT vibrator or the hardness of other rigid objects.

9 Claims, 7 Drawing Sheets

MEASURING SYSTEM FOR DETERMINING THE ELECTROMECHANICAL COUPLING CHARACTERISTICS OF A PZT VIBRATOR

BACKGROUND OF THE INVENTION

1. Field of the Invention

The invention is about a measuring system for determining the electromechanical coupling characteristics of a piezoceramic (PZT) vibrator, and more particularly to a system measuring bouncing height and time of a metal ball for determining the electromechanical coupling characteristics of a PZT vibrator or for determining the hardness of other rigid object.

2. Description of the Prior Art

When an object is placed on surface of a Langevin PZT vibrator vibrating in high frequency, the object is easily to leave up and to slip, which is called levitation phenomena of vibrators in physics. Traditionally, ultrasonic levitation is caused by a vibrator vibrating in ultrasonic frequency to disturb the air and then generate a radiation pressure field. If an object is placed in the pressure field, it would be levitated by the radiation pressure. As a result of decrease of contact force between the object and vibrating surface, the ultrasonic levitation can solve industrial abrasion and vibration issues.

However, it is hard to measure the contact status between the levitated object and the vibrator and to realize whether there is a point contact or a air gap. Prior researches apply several methods comprising using CCD camera to observe the levitation; measuring different required voltage of the vibrator to levitate objects with different weight; using Doppler laser analyzer to measure the gap between the levitated object and the vibrator and realize the contact status with quantification of data; or using non-contact opto-fiber displacement meter to directly measure the tiny vibration of the vibrator. No matter how, the mechanism is caused by the effect of piezoceramic material of a Langevin vibrator transforming the input electrical power into mechanical energy. The mechanical energy is presented in mechanical form and is the important issue of measurement.

SUMMARY OF THE INVENTION

One object of the invention is to provide a system of measuring the bouncing height and flying time of a metal ball, for applying the measured data to determine the electromechanical coupling characteristics of a PZT vibrator or the hardness of other rigid objects.

To achieve the object, the invention comprises:

an elastic-bouncing tester, which can load a metal ball and confine bouncing motion of the metal ball in the tester; wherein the elastic-bouncing tester comprises a transparent tube, and a Langevin PZT vibrator;

a driving circuit, which is powered to activate the bouncing motion of the metal ball in the elastic-bouncing tester, and the driving circuit comprises a function generator, a power amplifier, wherein the function generator generates a sine wave signal inputted to the power amplifier, and the power amplifier is activated to drive the Langevin PZT vibrator;

a height measuring circuit, which can measure the bouncing position of the metal ball in the elastic-bouncing tester, wherein the height measuring circuit comprises a photo-interrupter matrix, and a multiplexer, wherein the photo-interrupters matrix comprises at least twenty-four photo-interrupters made by a light emitting diode(LED) and photo-transistor, and the multiplexer is operated by employing 74LS244 tri-state-outputs octal buffer;

an instantaneous height indicator, which instantaneously shows the bouncing height of the metal ball in the elastic-bouncing tester in bouncing motion, wherein the instantaneous height indicator comprises a LED matrix comprising at least 24 LEDs, and a data latch circuit operated by employing 74LS373 latch IC;

a microprocessor, which processes, stores, and presents bouncing motion signal of the metal ball in the elastic-bouncing tester, wherein the microprocessor is operated by employing the microprocessor 8052;

a monitor, which shows the measured bouncing motion signal of the metal ball; and a push-button switch circuit, which provides functions in response to kinds of operation modes.

The system structure of the invention is able to measure the bouncing height and flying time of the metal ball, and to determine the electromechanical coupling characteristics of a PZT vibrator or the hardness of other rigid objects.

BRIEF DESCRIPTION OF THE DRAWINGS

The drawings disclose an illustrative embodiment of the present invention which serves to exemplify the various advantages and objects hereof, and are as follows.

DETAILED DESCRIPTION OF THE PREFERRED EMBODIMENT

Figure 1:
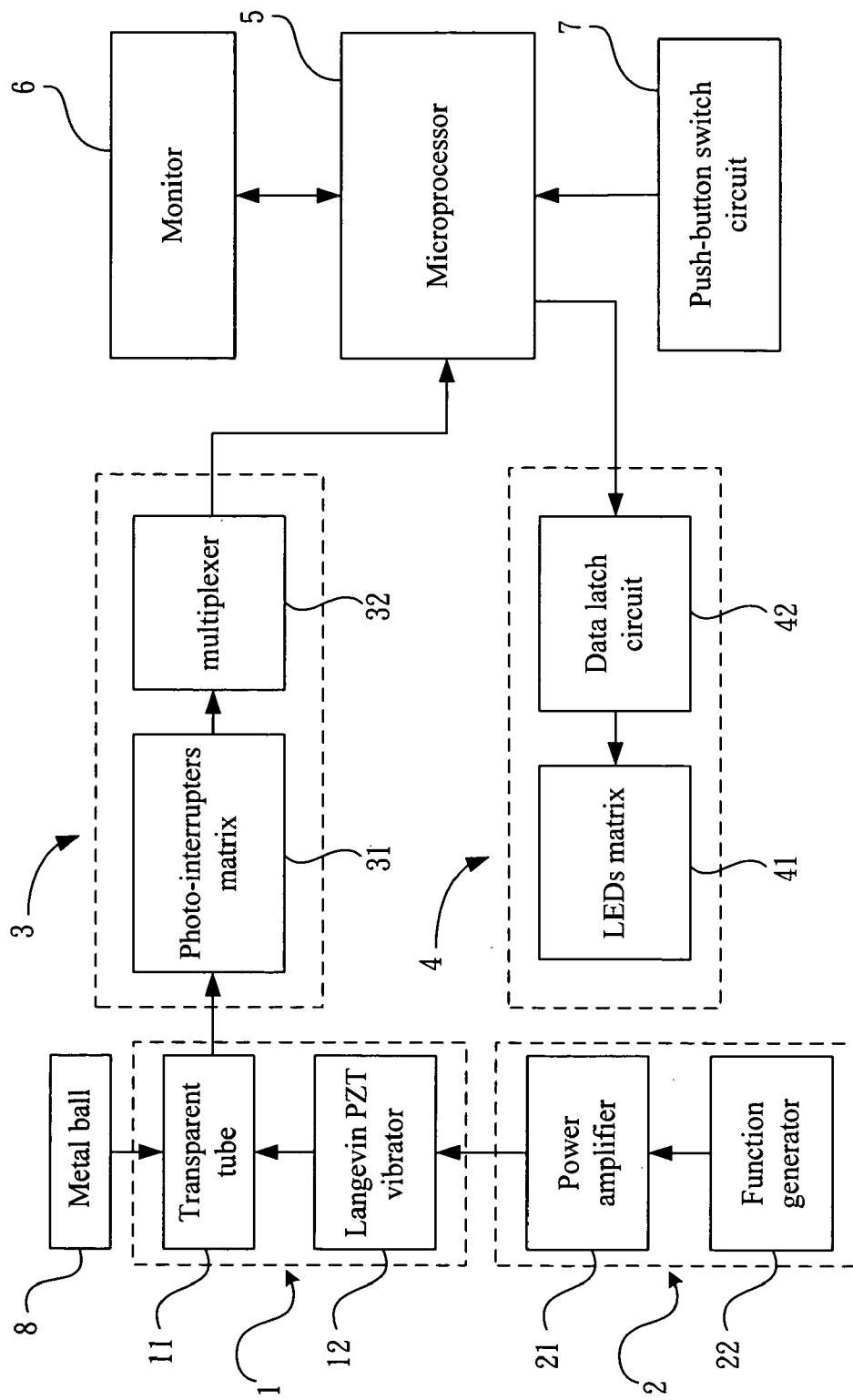
FIG. 1 is a perspective view of system structure of the invention.

FIG. 1 is a perspective view of system structure of the invention, comprising: an elastic-bouncing tester 1, which can load a metal ball 8 and confine bouncing motion of the metal ball 8 in the tester 1; wherein the elastic-bouncing tester 1 comprises a transparent tube 11, and a Langevin PZT vibrator 12;

a driving circuit 2, which is powered to activate the bouncing motion of the metal ball 8 in the elastic-bouncing tester 1, and the driving circuit comprises a function generator, a power amplifier, wherein the function generator generates a sine wave signal inputted to the power amplifier, and the power amplifier is activated to drive the Langevin PZT vibrator;

a height measuring circuit 3, which can measure the bouncing position of the metal ball 8 in the elastic-bouncing tester 1, wherein the height measuring circuit 3 comprises a photo-interrupters matrix 31, and a multiplexer 32, wherein the photo-interrupters matrix 31 comprises at least twenty-four photo-interrupters made by a light emitting diode(LED) and photo-transistor, and the multiplexer 32 is operated by employing 74LS244 tri-state-outputs octal buffer;

an instantaneous height indicator 4, which instantaneously shows the bouncing height of the metal ball 8 in the elastic-bouncing tester 1 in bouncing motion, wherein the instantaneous height indicator 4 comprises a LEDs matrix 41 comprising at least 24 LEDs, and a data latch circuit 42 operated by employing 74LS373 latch IC;

a microprocessor 5, which processes, stores, and presents bouncing motion signal of the metal ball 8 in the elastic-bouncing tester 1, wherein the microprocessor 5 is operated by employing the microprocessor 8052;

a monitor 6, which shows the measured bouncing motion signal of the metal ball 8; and a push-button switch circuit 7, which provides functions in response to kinds of operation modes.

In the measuring system for determining the electromechanical coupling characteristics of a PZT vibrator, there is the photo-interrupters matrix 31 vertically set on the Langevin PZT vibrator 12, wherein the photo-interrupters matrix 31 comprises a transparent tube 11 made in glass or other transparent materials, and the metal ball 8 is inside the transparent tube 11. The transparent tube 11 allows near-infrared rays going through it and into a receiving device. When the Langevin PZT vibrator 12 is actuated by AC power source via the driving circuit 2, the metal ball 8 bounces in the transparent tube 11, and the motion is divided into three modes of:

contact mode: the metal ball 8 impacts the Langevin PZT vibrator 12;

bouncing mode: the metal ball 8 bounces upward; and falling mode: the metal ball falls downward.

In contact mode, the metal ball 8 interrupts the lowest position photo-interrupter of the photo-interrupters matrix 31, which makes the output $V_{C1}$ of the interrupted photo-interrupter in high voltage level, $V_{High}$, and other outputs $V_{C2}, V_{C3}, \ldots, V_{C24}$ of photo-interrupters remain in low voltage level, $V_{Low}$. In bouncing mode, the metal ball 8 sequentially interrupts the photo-interrupter of the photo-interrupters matrix, and sequentially makes $V_{C2}, V_{C3}, \ldots, V_{C24}$ in high voltage level, $V_{High}$. In falling mode, the metal ball 8 falls from the highest position, N, of itself by the end of bouncing mode, and the mode is ended when the metal ball 8 impacts the Langevin PZT vibrator 12. In falling mode, the metal sequentially interrupts the photo-interrupter of the photo-interrupters matrix, and sequentially makes $V_{CN-1}, V_{CN-2}, \ldots, V_{C1}$ in high voltage level, $V_{High}$.

The voltage signal caused by the bouncing motion of the metal ball 8 shows on output of the photo-interrupters matrix 31, and transfers to the 8052 microprocessor 5 via the 3 byte-to-1 byte multiplexer 32, and the select line of the multiplexer 32 is controlled by the 8052 microprocessor 5.

The 8052 microprocessor 5 measures the bouncing height h in response to bouncing motion from the multiplexer 32, and calculates contact time $t_c$ in contact mode, bouncing upward time $t_{up}$ in bouncing mode, and falling downward time $t_{fall}$ in falling mode. Meanwhile, the 8052 microprocessor 5 instantaneously indicates the bouncing height of the metal ball 8 via the instantaneous height indicator 4, wherein the instantaneous height indicator 4 comprises the data latch circuit 42 driving the LEDs matrix 41, and the LEDs matrix 41 shows the height information.

In each bouncing motion, it generates information comprising bouncing height h, contact time $t_c$, bouncing upward time $t_{up}$, and falling downward time $t_{fall}$, which are stored in the random-access memory of 8052 microprocessor 5, and can be transferred to personal computer via RS-232 serial port for analyzing the bouncing motion.

The 8052 microprocessor 5 can store twenty data in its random-access memory, and each datum occupies 8 byte memory. If it is needed to store more data, an extended random-access memory can be assembled to extend capacity of memory. When the space of memory of the 8052 microprocessor 5 is full, user can use the monitor 6 to display the bouncing information of the metal ball 8 for reading data.

The monitor 6 and the push-button switch circuit 7 form an user interface of the system. The monitor 6 can show the bouncing data, and text or hint in response to each operating mode of the system. The push-button switch circuit 7 provides buttons of:

(1) reset: for resetting the system and restart the measurement;

(2) start/stop: for starting or stopping measuring the metal ball 8;

(3) UP: for reading the bouncing data stored in the memory and showing it on the monitor 6 in sequence from the first datum to the twentieth datum; and (4) DOWN: for reading the bouncing data stored in the memory and showing it on the monitor 6 in sequence from the twentieth datum to the first datum.

Figure 2:
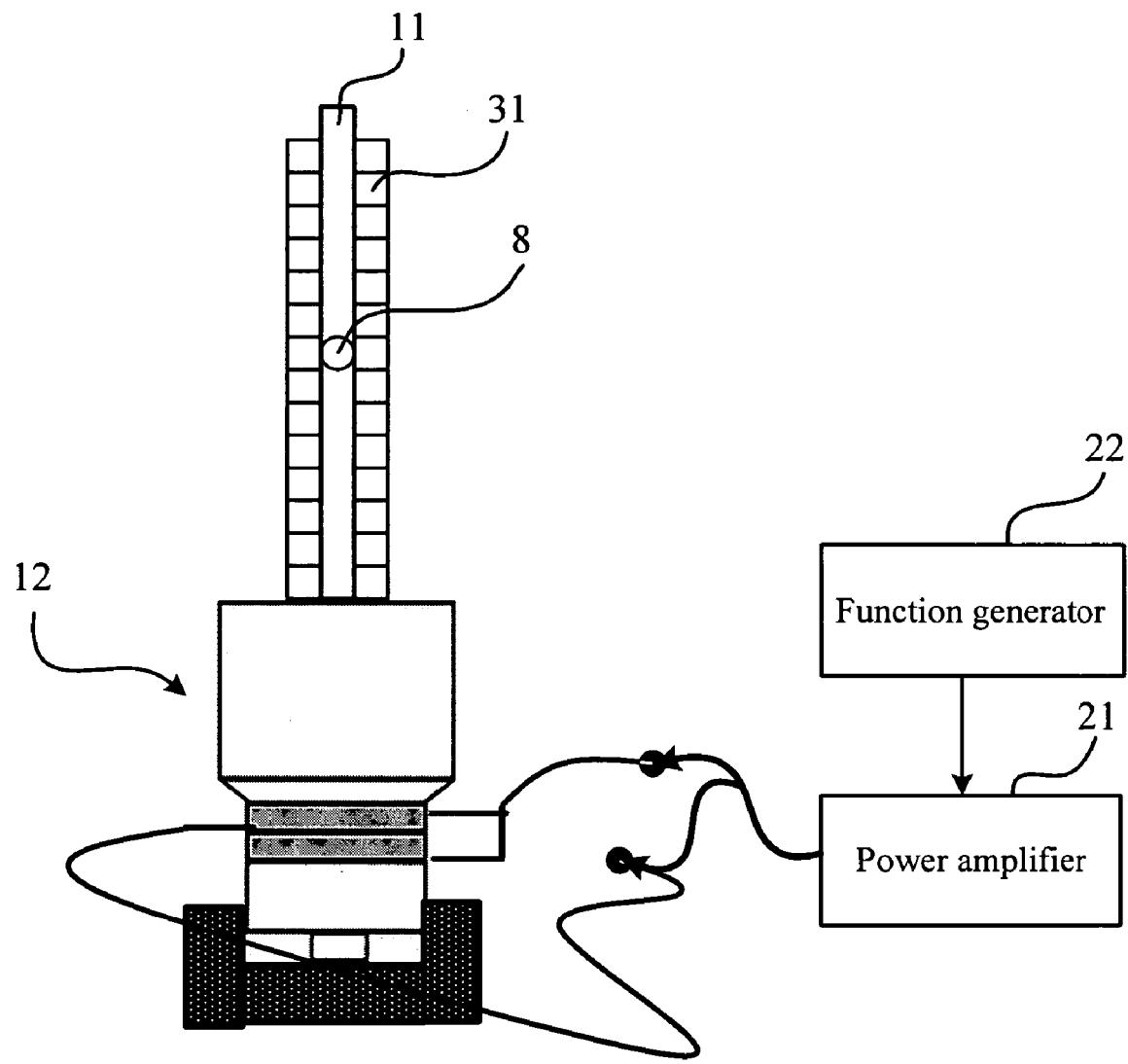
FIG. 2 is a perspective view of custom structure embodiment of the invention.

FIG. 2 is a perspective view of custom structure embodiment of the invention. The function generator 22 generates a sine wave signal to the power amplifier 21 for driving the Langevin PZT vibrator 12, then the metal ball 8 bounces in the transparent tube 11. The photo-interrupters matrix 31 can measure the bouncing position of the metal ball 8 and generate output signal to a signal processing circuit with core of 8052 microprocessor 5 for processing, storing, and showing the bouncing information.

Figure 3:
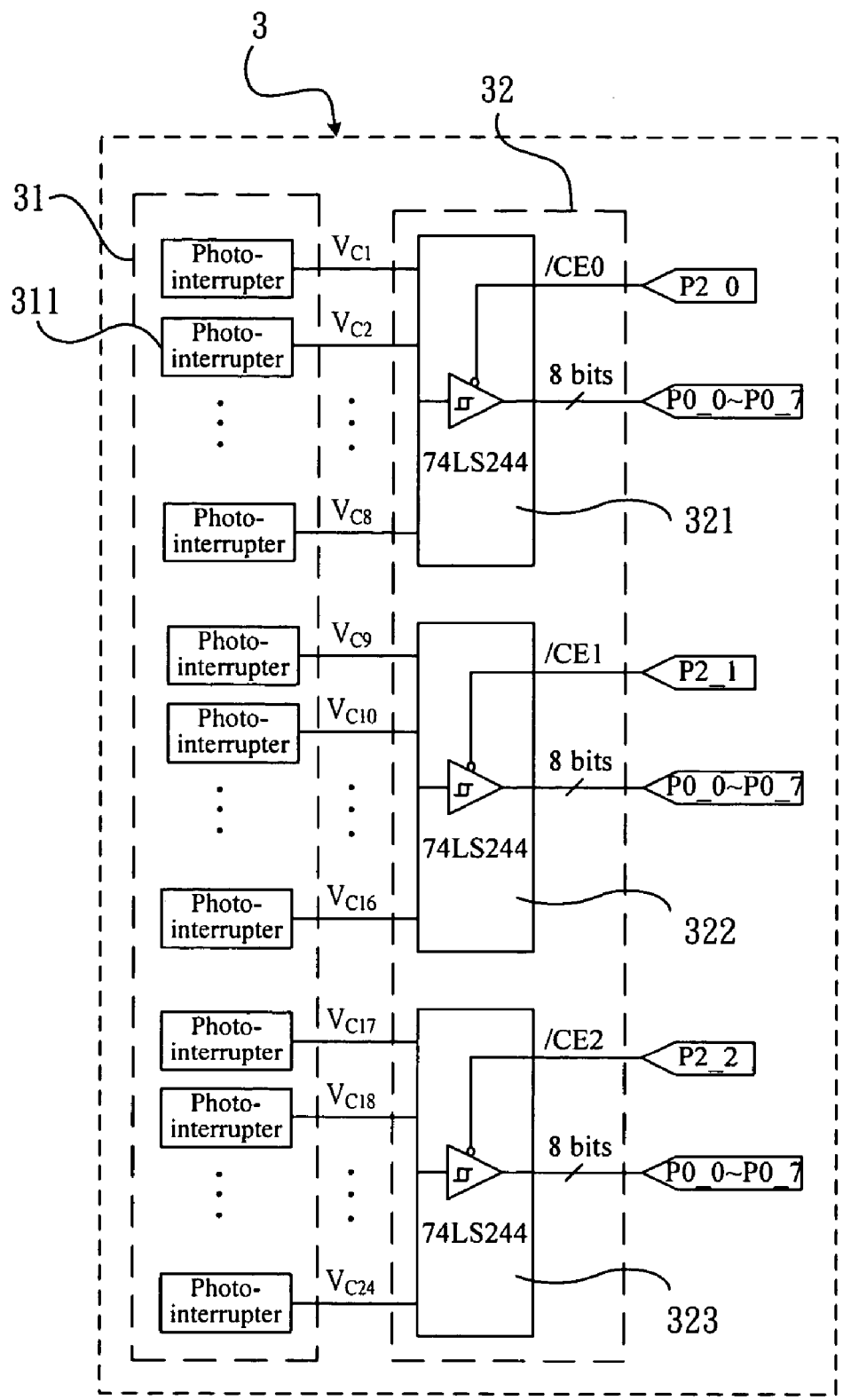
FIG. 3 is a perspective view of height measuring circuit of the invention.

FIG. 3 is a perspective view of height measuring circuit 3 of the invention. The height measuring circuit 3 comprises the photo-interrupters matrix 31 and the multiplexer 32. The photo-interrupters matrix 31 comprises twenty-four photo-interrupters 311, and the output $V_{C1}, V_{C2}, \ldots, V_{C24}$ of each photo-interrupter 311 is coupled to the 3 byte-to-1 byte multiplexer 32 made of three 74LS244 tri-state-outputs octal buffers. The select line /CE0 of the multiplexer 32 is controlled by the output pin P2_0 of 8052 microprocessor 5. When the pin P2_0 is in low voltage level, the signals of the outputs $V_{C1} \sim V_{C8}$ of the photo-interrupter 311 are transferred to the pin P0_0~P0_7 of the 8052 microprocessor 5 via the 74LS244 tri-state-outputs octal buffer 321. Similarly, the select line /CE1 is controlled by the output pin P2_1. When the pin P2_1 is in low voltage level, the signals of the outputs $V_{C9} \sim V_{C16}$ of the photo-interrupter 311 are transferred to the pin P0_0~P0_7 of the 8052 microprocessor 5 via the 74LS244 tri-state-outputs octal buffer 322. The select line /CE2 is controlled by the output pin P2_2. When the pin P2_2 is in low voltage level, the signals of the outputs $V_{C17} \sim V_{C24}$ of the photo-interrupter 311 are transferred to the pin P0_0~P0_7 of the 8052 microprocessor 5 via the 74LS244 tri-state-outputs octal buffer 323.

Figure 4:
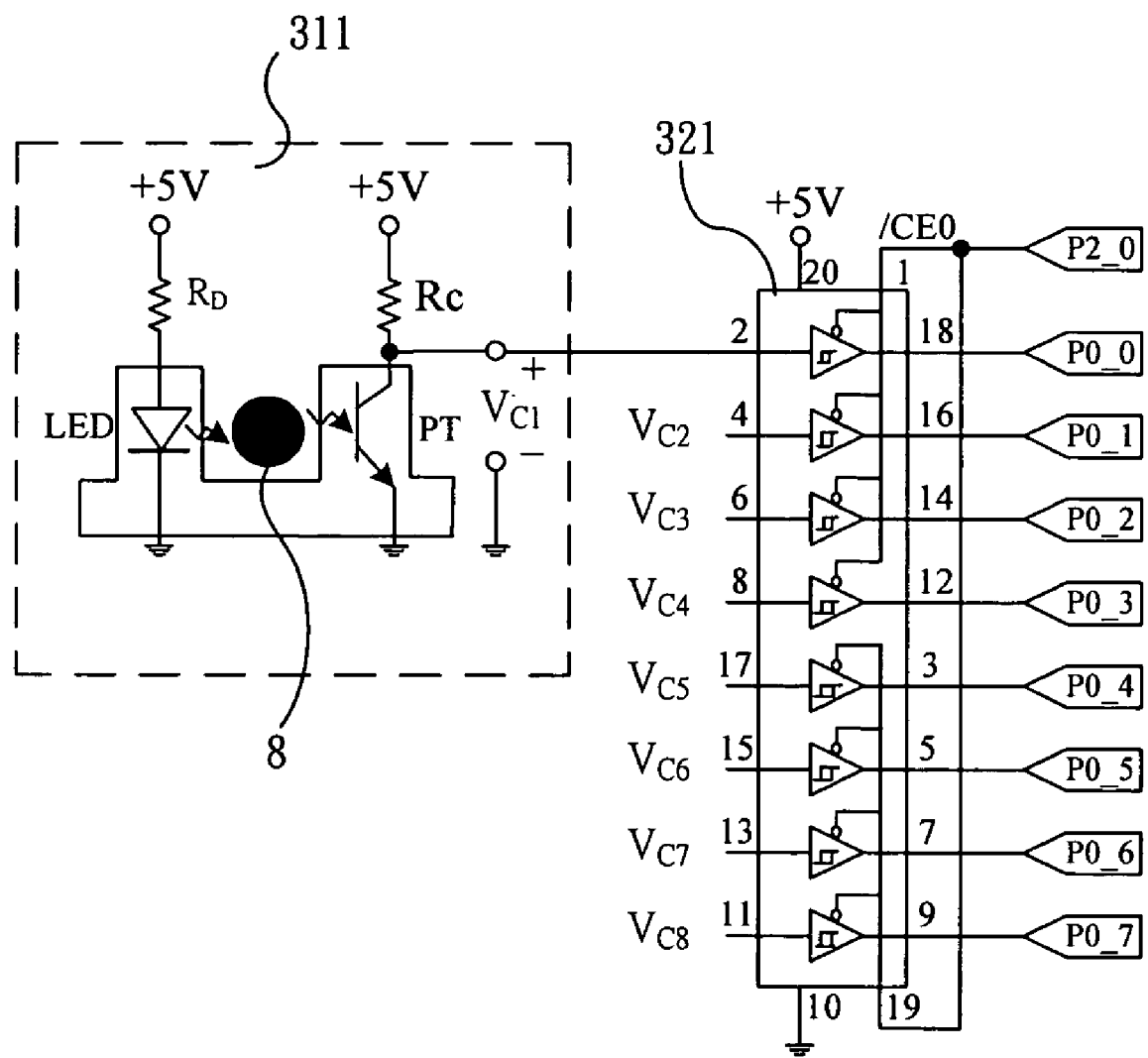
FIG. 4 is a perspective view of an embodiment of partial height measuring circuit of the invention.

FIG. 4 is a perspective view of an embodiment of partial height measuring circuit of the invention.

The photo-interrupter 311 is made of the infrared ray LED and the photo-transistor PT. In +5V power supply circumstance, properly choosing a current limiting resistor $R_D$ and a bias resistor $R_C$ to make the light of the infrared ray LED enough to drive the photo-transistor PT into the saturation region and generate a low voltage output, which means the output $V_{C1}$ of the photo-interrupter 311 is in low voltage level. When the metal ball 8 completely block the light of the infrared ray LED, the photo-transistor PT is operated in the cut-off region and generates a high voltage output, which means the output $V_{C1}$ of the photo-interrupter 311 is in high voltage level. The output $V_{C1}$ of the photo-interrupter 311 is connected to the input of the 74LS244 tri-state-outputs octal buffer 321.

The 74LS244 tri-state-outputs octal buffer 321 is a TTL IC comprising eight tri-state outputs. The output $V_{C1}$ of the photo-interrupter 311 is connected to the second pin of the input of the 74LS244 tri-state-outputs octal buffer 321, and the outputs $V_{C2}, V_{C3}, \ldots, V_{C8}$ of the photo-interrupter 311 are separately connected to forth, sixth, eighth, seventeenth, fifteenth, thirteenth, and eleventh pin of the input of the 74LS244 tri-state-outputs octal buffer 321. The control pin /CE0 of the tri-state output of the 74LS244 tri-state-outputs octal buffer 321 is connected to the pin P2_0 of the 8052 microprocessor 5. When the /CE0 is in low voltage level, the eight signals of input of the 74LS244 tri-state-outputs octal buffer 321 are transferred to the P0_0~P0_7 of the 8052 microprocessor 5, as if the switch is in ON status; on the contrary, when the /CE0 is in high voltage level, the output of the 74LS244 tri-state-outputs octal buffer 321 presents high-impedance phenomenon, as if the switch is in OFF status.

Figure 5:
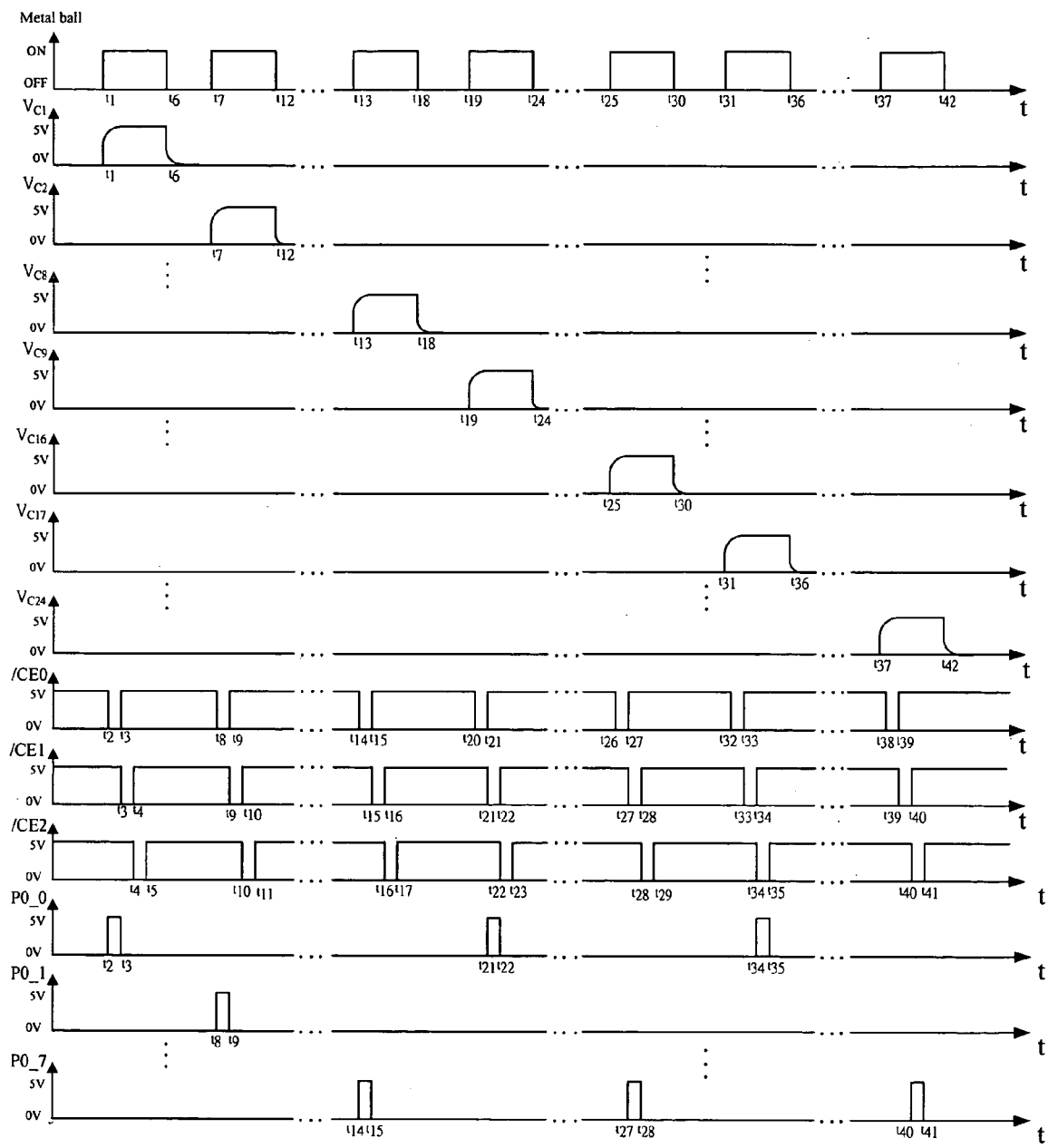
FIG. 5 is a perspective view of timing sequences of the invention.

FIG. 5 is a perspective view of timing sequences of the invention, which shows relevant timing sequences of the metal ball 8, outputs $V_{C1}$~$V_{C24}$ of the photo-interrupters matrix 31, select lines /CE0, /CE1, /CE2 of the multiplexer 32, and the P0_0~P0_7 of the 8052 microprocessor 5 in bouncing motion. In time period from $t_1$ to $t_6$, the metal ball 8 is in ON state, which means the metal ball 8 is positioned in the first photo-interrupter 311, and makes the output of $V_{C1}$ in high voltage level, 5V, while $V_{C2}$~$V_{C24}$ are in low voltage level, 0V. In time period from $t_2$ to $t_3$, the select line /CE0 of the multiplexer 32 is in low voltage level, 0V, which makes the high voltage level, 5V, of the $V_{C1}$ show on P0_0, while P0_1~P0_7 are in low voltage level, 0V. In time period from $t_3$ to $t_4$, and from $t_4$ to $t_5$, the select lines /CE1, and /CE2 are separately in low voltage level, 0V, while P0_1~P0_7 are in low voltage level, 0V. It can seen that only the $V_{C1}$ is in high voltage level, 5V, and $V_{C2}$~$V_{C24}$ are all in low voltage level, 0V.

In time period from $t_7$ to $t_{12}$, the metal ball 8 is positioned in the second photo-interrupter 311, and makes the output of $V_{C2}$ in high voltage level, 5V, while $V_{C1}$, $V_{C3}$~$V_{C24}$ are in low voltage level, 0V. In time period from $t_8$ to $t_9$, the select line /CE0 of the multiplexer 32 is in low voltage level, 0V, which makes the high voltage level, 5V, of the $V_{C2}$ show on P0_1, while P0_0, P0_2~P0_7 are in low voltage level, 0V. In time period from $t_9$ to $t_{10}$, and from $t_{10}$ to $t_{11}$, the select lines /CE1, and /CE2 are separately in low voltage level, 0V, while P0_1~P0_7 are in low voltage level, 0V. By the same principle, when the metal ball 8 is positioned in a certain photo-interrupter, output of the certain photo-interrupter is in high voltage level, 5V. For example, in time period from $t_{13}$ to $t_{18}$, the output of $V_{C8}$ is in high voltage level, 5V. In time period from $t_{14}$ to $t_{15}$, the select line /CE0 of the multiplexer 32 is in low voltage level, 0V, which makes the high voltage level, 5V, of the $V_{C8}$ show on P0_7, while P0_0~P0_6 are in low voltage level, 0V.

In time period from $t_{19}$ to $t_{24}$, the metal ball 8 is positioned in the ninth photo-interrupter 311, and makes the output of $V_{C9}$ in high voltage level, 5V. In time period from $t_{21}$ to $t_{22}$, the select line /CE1 is in low voltage level, 0V, which makes the P0_0 in high voltage level, 5V, while P0_1~P0_7 are in low voltage level, 0V. By the same principle, in time period from $t_{25}$ to $t_{30}$, the metal ball 8 is positioned in the sixteenth photo-interrupter 311, and makes the output of $V_{C16}$ in high voltage level, 5V. In time period from $t_{27}$ to $t_{28}$, the select line /CE1 is in low voltage level, 0V, which makes the high voltage level, 5V, of the $V_{C16}$ show on P0_7, while P0_0~P0_6 are in low voltage level, 0V. In time period from $t_{31}$ to $t_{36}$, the metal ball 8 is positioned in the seventeenth photo-interrupter 311, and makes the output of $V_{C17}$ in high voltage level, 5V. In time period from $t_{34}$ to $t_{35}$, the select line /CE2 is in low voltage level, 0V, which makes the P0_0 in high voltage level, 5V, while P0_1~P0_7 are in low voltage level, 0V. In time period from $t_{37}$ to $t_{42}$, the metal ball 8 is positioned in the twenty-fourth photo-interrupter 311, and makes the output of $V_{C24}$ in high voltage level, 5V. In time period from $t_{40}$ to $t_{41}$, the select line /CE2 is in low voltage level, 0V, which makes the high voltage level, 5V, of the $V_{C24}$ show on P0_7, while P0_0~P0_6 are in low voltage level, 0V.

Since the select lines /CE0, /CE1, /CE2 are separately controlled by the P2_0, P2_1, P2_2 of the 8052 microprocessor 5, it can apply a program to determine the corresponding input signals of P0_0~P0_7, and then the system can collect complete output signals of the twenty-four photo-interrupters 311, and transfer the output signals into bouncing height data of the metal ball 8.

Further, there is only one select line of /CE0, /CE1, /CE2 of the multiplexer 32 can be allowed to be in low voltage level, 0V, which ensures the output signal of the photo-interrupter being read correctly. Frequencies of switching the control signal of /CE0, /CE1, /CE2 are determined by the program of the 8052 microprocessor 5. Since the multiplexer 32 has to separately and continuously switch the /CE0, /CE1, /CE2 to low voltage level, 0V, in a switching cycle for completely reading the bouncing height signal of the metal ball 8 in the photo-interrupters matrix 31, the length of the switching cycle has to be shorter than the timing intervals of the metal ball 8 from one photo-interrupter to next photo-interrupter, to ensure the system can correctly measure the bouncing height of the metal ball 8, the fastest speed can be calculated according to free falling equation:

$$\tfrac{1}{2}mv^2 = mgh, \quad v=(2\,gh)^{1/2}$$

Wherein the v means the instantaneous velocity of the metal ball 8 when it impacts the PZT vibrator 12, or levitates the surface of the PZT vibrator 12, with unit of cm/sec; the g is the acceleration of gravity, which is equal to 980 cm/sec$^2$; the h is the bouncing height of the metal ball with unit of cm. In one embodiment, the h is equal to 17.907 cm, the v is equal to 187.34 cm/sec, and the diameter $\Phi$ of the metal ball 8 is 0.477 cm, thus, the shortest time the photo-interrupter 311 blocked by the metal ball 8 is:

$$t_{min}=\Phi/v=2.55\ ms$$

Thus, the length of the switching cycle of select lines /CE0, /CE1, /CE2 has to shorter than the $t_{min}$ to measure the bouncing height of the metal ball 8.

Figure 6:
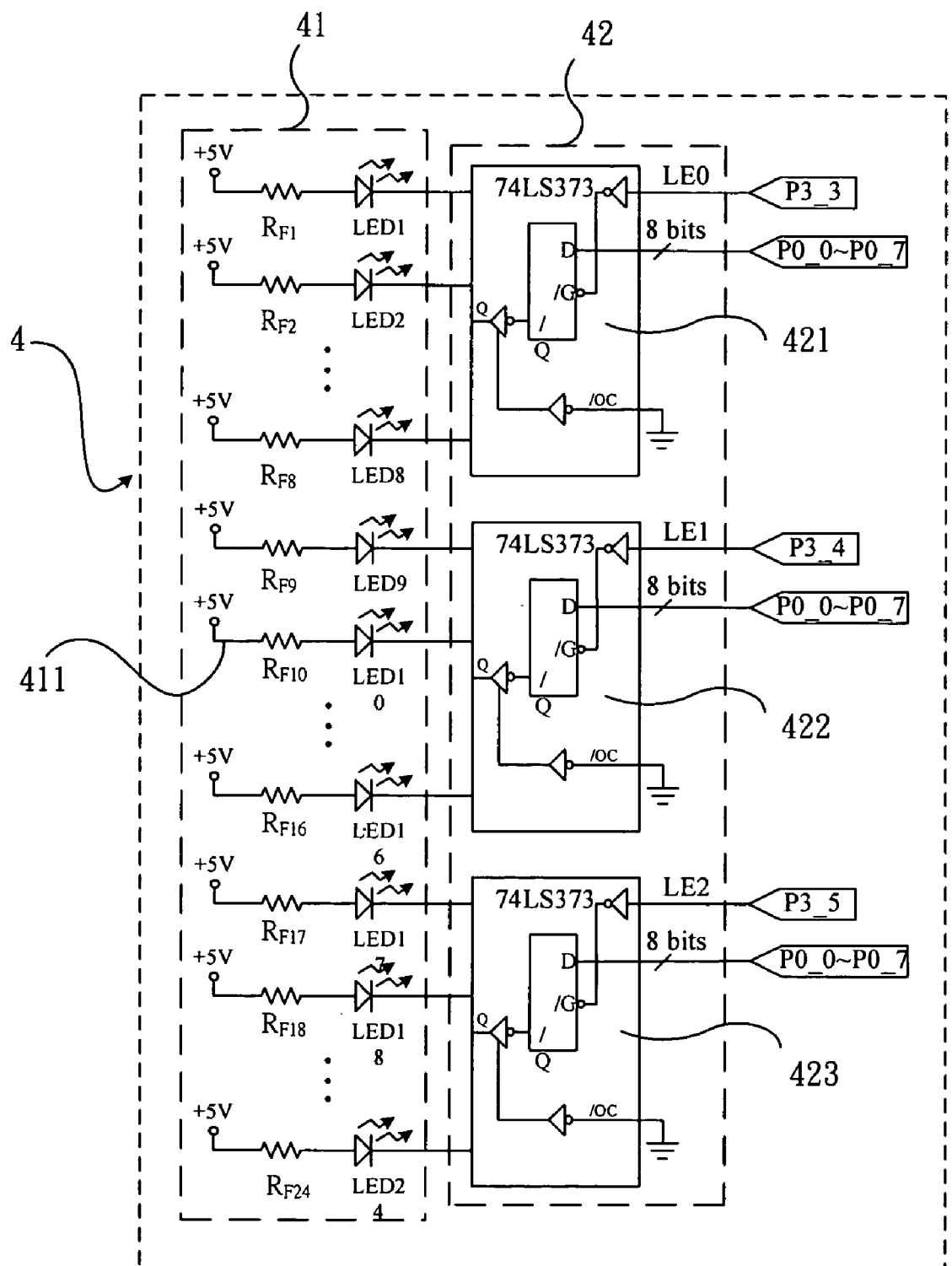
FIG. 6 is a perspective view of instantaneous height indicator of the invention.

FIG. 6 is a perspective view of instantaneous height indicator of the invention. The instantaneous height indicator 4 comprises the LEDs matrix 41 and the data latch circuit 42.

The instantaneous height indicator 4 drives twenty-four LEDs 411, LED1~LED24. Indicating an instantaneous height means that the position of the metal ball 8 in the photo-interrupters matrix 31 would instantaneously show on the LEDs matrix 41, thus the LEDs matrix 41 can be applied as an auxiliary tool to observe the bouncing height of the metal ball 8. The data latch circuit 42 comprises three 74LS373 latch ICs, which separately stores the bouncing height signals from the P0_O~P0_7 of the 8052 microprocessor 5 in 74LS373 latch IC 421, 74LS373 latch IC 422, and 74LS373 latch IC 423 in response to the high-level-pulse latch signals of P3_3, P3_4, and P3_5. Thus the LEDs matrix 41 connected to the data latch circuit 42 can show the position of the metal ball 8 in bouncing motion. In the LEDs matrix 41, the LED1~LED8 are connected to the outputs of the 74LS373 latch IC 421, the LED9~LED16 are connected to the outputs of the 74LS373 latch IC 422, the LED17~LED24 are connected to the outputs of the 74LS373 latch IC 423, and limiting-current resistors $R_{F1} \sim R_{F24}$ are separately connected to LED1~LED24 in series for controlling the brightness of the LED 411.

Figure 7:
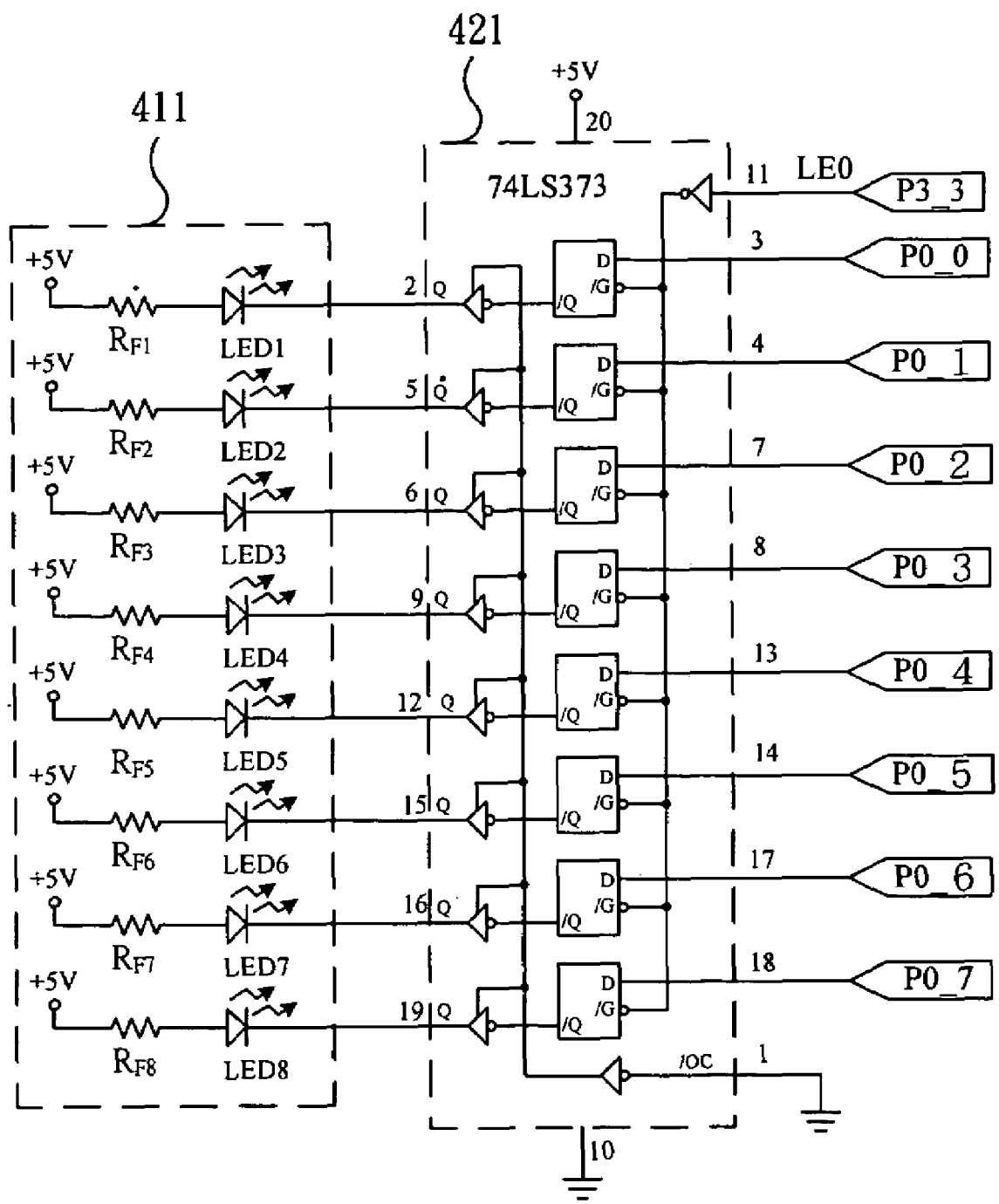
FIG. 7 is a perspective view of an embodiment of partial instantaneous height indicator of the invention.

FIG. 7 is a perspective view of an embodiment of partial instantaneous height indicator of the invention. The 74LS373 latch IC 421 drives the LEDs matrix 41 comprising eight LEDs, wherein the latch control pin LEO is connected to the P3_3 of the 8052 microprocessor 5, the data input D is connected to the P0_0~P0_7, and the outputs Q of the 74LS373 latch IC are connected to the LED1~LED8.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A measuring system for determining electromechanical coupling characteristics of a PZT vibrator which comprises:
   an elastic-bouncing tester, which can load an object and confine bouncing motion of the object in the elastic-bouncing tester, said elastic-bouncing tester including a PZT vibrator;
   a driving circuit, which is powered to activate the bouncing motion of the object in the elastic-bouncing tester;
   a height measuring circuit, which can measure the bouncing position of the object in the elastic-bouncing tester;
   an instantaneous height indicator, which instantaneously shows the bouncing height of the object in the elastic-bouncing tester in bouncing motion;
   a microprocessor, which processes, stores, and presents bouncing motion signal of the object in the elastic-bouncing tester; and
   a monitor, which shows the measured bouncing motion signal of the object; and
   a push-button switch circuit, which provides functions in response to kinds of operation modes.

2. The system of claim 1, wherein the object is a metal ball.

3. The system of claim 1, wherein the elastic-bouncing tester comprises a transparent tube, and a PZT vibrator.

4. The system of claim 3, wherein the material of the transparent tube can be glass or other transparent materials.

5. The system of claim 3, wherein the PZT vibrator is a Langevin PZT Vibrator.

6. The system of claim 3, wherein the driving circuit comprises a function generator and a power amplifier, wherein the function generator generates a sine wave signal inputted to the power amplifier, and the power amplifier is activated to drive the Langevin PZT vibrator.

7. The system of claim 1, wherein the height measuring circuit comprises a photo-interrupters matrix and a multiplexer.

8. The system of claim 7, wherein the photo-interrupters matrix is made by a light emitting diode and a phototransistor.

9. The system of claim 1, wherein the instantaneous height indicator comprises an LED matrix and a data latch circuit.

* * * * *